US00PP35180P3

(12) United States Plant Patent
Ruter

(10) Patent No.: US PP35,180 P3
(45) Date of Patent: May 23, 2023

(54) ***THUJA* PLANT NAMED 'RUTTHU5'**

(50) Latin Name: *Thuja occidentalis*
Varietal Denomination: RutThu5

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/854,234

(22) Filed: Jun. 30, 2022

(65) Prior Publication Data

US 2023/0007823 P1 Jan. 5, 2023

Related U.S. Application Data

(60) Provisional application No. 63/217,004, filed on Jun. 30, 2021.

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00; A01H 5/12; A01H 6/00
See application file for complete search history.

(56) References Cited

PUBLICATIONS

Canadian Food Inspection Agency retrieved on Aug. 2, 2022 at https://inspection.canada.ca/english/plaveg/pbrpov/cropreport/ced/app00012410e.shtml, 2 pp. (Year: 2022).*
First Editions Shrubs & Trees Tall Guy Arbovitae retrieved on Aug. 2, 2022 at https://firsteditionsplants.com/product/tall-guy-arborvitae/, 4 pp. (Year: 2022).*
Trademark Electronic Search System (TESS) retrieved on Aug. 2, 2022 at https://tmsearch.uspto.gov/bin/showfield?f=doc&state=4801:ykep6.3.1, 2 pp. (Year: 2022).*
License Agreement dated Mar. 30, 2020 (financial and personal information redacted).

* cited by examiner

*Primary Examiner* — June Hwu
(74) *Attorney, Agent, or Firm* — Thomas Horstemeyer, LLP

(57) ABSTRACT

A new and distinct cultivar of *Thuja* plant named 'RutThu5', characterized by its nice, columnar form, dark green foliage that does not have chartreuse tips like *Thuja occidentalis* 'Emerald Green'. 'RutThu5' can be grown with one cutting per pot compared to the industry standard of three cuttings per pot, and has similar growth rate in containers and field as three-cutting plants of 'Emerald Green'. The new 'RutThu5' has demonstrated cold hardiness to about −34° F. in trials conducted in Minnesota.

2 Drawing Sheets

CROSS-REFERENCE TO RELATED APPLICATIONS

Figure 1:
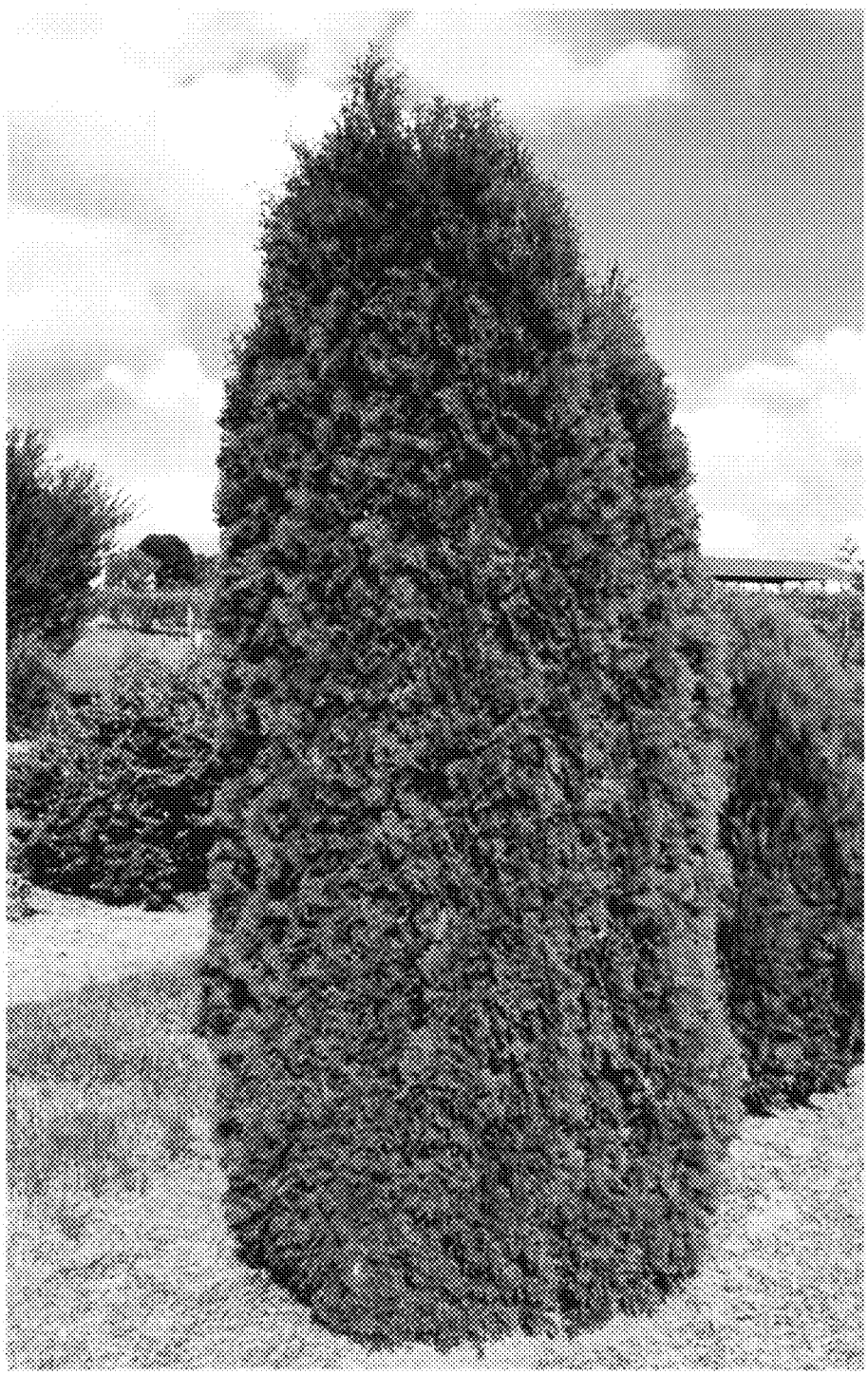

This application claims priority to U.S. provisional application titled "Thuja PLANTS NAMED 'RutThu2', 'RutThu3', 'RutThu4', and 'RutThu5'" having Ser. No. 63/217,004, filed on Jun. 30, 2021, which is entirely incorporated herein by reference.

Botanical designation: *Thuja occidentalis.*

Cultivar denomination 'RutThu5'.

BACKGROUND OF THE INVENTION

The present invention relates to a new and distinct cultivar of *Thuja*, botanically know as *Thuja occidentalis*, and hereinafter referred to by the cultivar name 'RutThu5'.

The new *Thuja* cultivar 'RutThu5' is a product of open pollination of *Thuja occidentalis* 'Fastigiate' (unpatented). The open-pollinated seeds were obtained in 2011 from Estonia. Seedlings were planted in Watkinsville in 2014. The new cultivar 'RutThu5' was selected for its upright, oval, columnar growth form, darker green color than *Thuja occidentalis* 'Emerald Green', one cutting per pot growth with similar growth rate to three-cutting plants, and cold hardiness to about −34° F. in trials conducted in Minnesota.

Asexual reproduction of the new *Thuja* 'RutThu5' using hardwood cuttings has been continued in Watkinsville, Ga. since 2015. Observations of the resulting progeny have shown that the unique features of this new *Thuja* 'RutThu5' are stable and reproduced true to type in successive generations. The new 'RutThu5' has also been grown in MN.

SUMMARY OF THE INVENTION

The new *Thuja* cultivar 'RutThu5' has not been observed under all possible environmental conditions. The phenotypes may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Thuja* cultivar named 'RutThu5'. In combination, these traits set 'RutThu5' apart from all other existing varieties of *Thuja* known to the inventors.

1. upright, oval, columnar growth form;
2. darker green color than *Thuja occidentalis* 'Emerald Green' and new growth that does not have chartreuse color of new growth of 'Emerald Green';
3. ability to be grown with one cutting per pot, compared to industry standard of three-cuttings per pot for cultivars like 'Emerald Green';
4. similar growth rate for one-cutting plants in the field and containers as compared to three-cutting plants of 'Emerald Green';
5. cold hardiness to about −34° F. in trials conducted in Minnesota.

Plants of the 'RutThu5' can be compared to similar cultivar *Thuja occidentalis* 'Emerald Green' (unpatetend) and differs from 'Emerald Green' in that 'RutThu5' has a more columnar form than 'Emerald Green', which is more conical. The foliage of 'RutThu5' is also darker green and does not have the chartreuse new growth of 'Emerald Green'. 'Emerald Green' is grown from three cuttings, but the new 'RutThu5' can be grown from one cutting per pot, but the one cutting plants have a similar growth rate in the field and containers as the three-cutting plants of 'Emerald Green'. Male parent plant is not conclusively known, so comparison data is not available. The new *Thuja* 'RutThu5' can also be compared to female parent *Thuja occidentalis* 'Fastigiate' (female parent) in that height to width ratio of 'RutThu5' is 2.1 compared to approximately 6.0 for 'Fastigiate'.

BRIEF DESCRIPTION OF THE PHOTOGRAPHS

The accompanying, colored photographic illustrations show the overall appearance and distinct characteristics of the new cultivar *Thuja* 'RutThu5' showing the colors as true as possible. Colors in the photographs may differ slightly from the color values cited in the detailed botanical description. The photographs were taken around June, 2021 of plants grown outdoors in Watkinsville, Ga.

The photograph labeled FIG. 1 depicts a side view of a typical 7-year-old 'RutThu5' plant showing the upright, columnar form and features.

Figure 2:
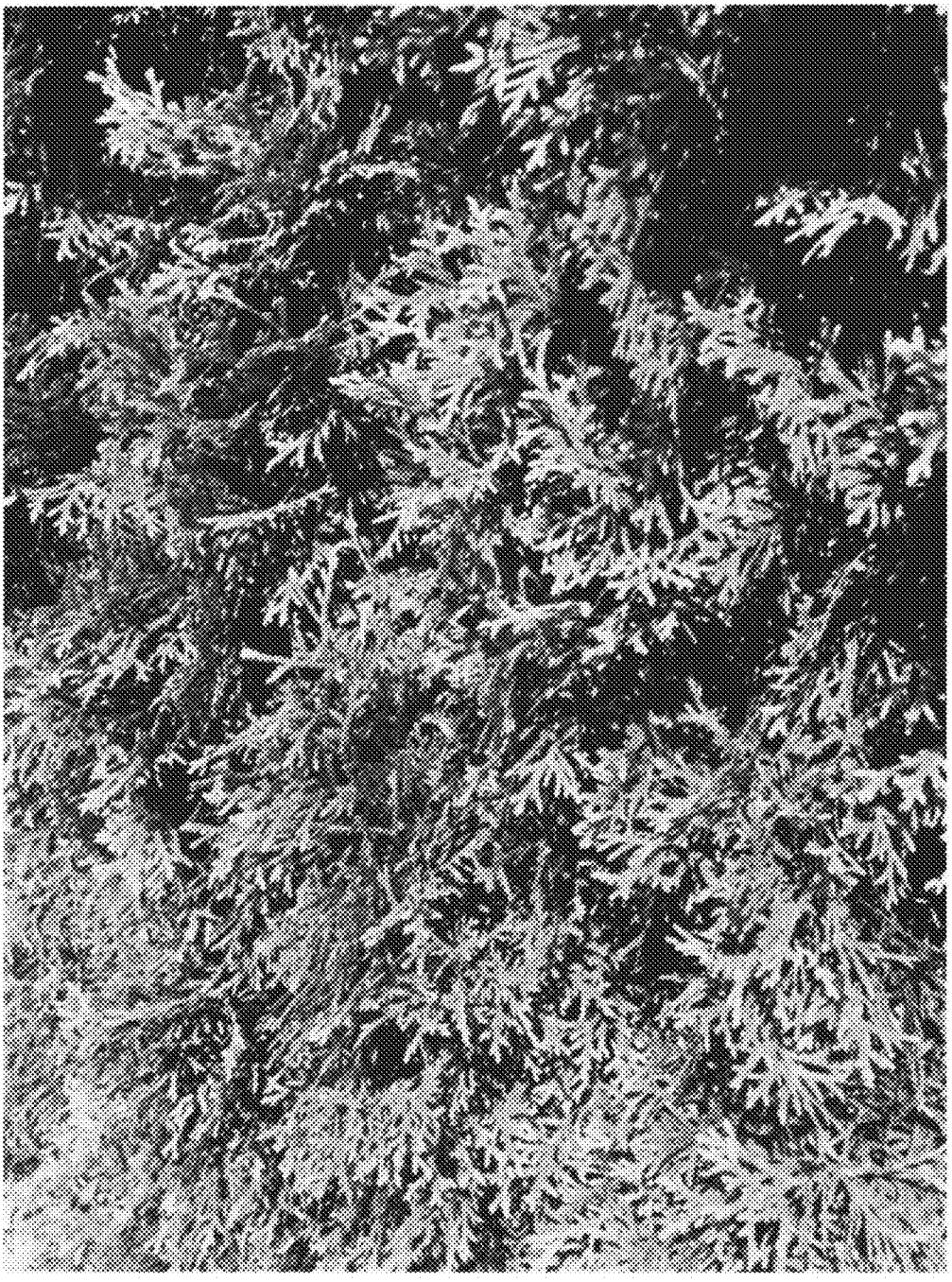

The photograph labeled FIG. 2 depicts a close-up view of the branches and needles of a typical 7-year-old 'RutThu5' plant showing the dark green color and lack of chartreuse-coloring on new growth.

DETAILED BOTANICAL DESCRIPTION

The following traits have been consistently observed in the original plants of the new varieties and in asexually propagated progeny grown in Watkinsville, Ga., (and some in MN) and, to the best knowledge of the inventors, their combination forms the unique characteristics of the new variety 'RutThu5'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Thuja* cultivar named 'RutThu5'. Data were collected from a horticulture farm in Watkinsville, Ga. from 6-year-old plants. The average low temperatures ranged from about 20° F. to 30° F. in the winter and about 90° F. to 100° F. in summer.

Botanical classification: *Thuja* 'RutThu5'.

Commercial classification: Ornamental conifer.

Parentage: Open pollination of *Thuja occidentalis* 'Fastigiate' by unknown pollen parents.

Growth and propagation:

*Propagation type*.—Terminal or sub-terminal hardwood cuttings.

*Growth rate*.—Moderate to fast.

*Root description*.—Typically about 2-6 roots arising from the base of the cuttings.

*Rooting habit*.—Good.

Plant description:

*Habit*.—Of 6-year-old plant in field — upright oval, columnar.

*Usage*.—Various uses, including landscaping, ornamental, container, border, hedge, and mass planting.

*Vigor*.—Good.

*Size of 4-year-old plant*.—A. Height: From soil level to top of plant, about 64 inches (about 114 inches for 6-year-old plant). B. Width: About 28 inches (about 54 inches for 6-year-old-plant). C. Ratio: About 2.3.

*Branch/stem (terminal tuft)*.—A. Quantity: Numerous. B. Length: About 6-13 cm. C. Base Diameter (year 2): About 4-5 mm at 15 cm from tip. D. Branch angle: About variable from 0 to about 65° from center. E: Odor (of bruised stem): Mild evergreen scent. F. Internode length: About 12-25 mm (about 5 internodes per sample). G: Color (R.H.S.): (At ½ year) Yellow Green 154B to Greyed-orange 177B. H: Strength of lateral branches: Good. I: Pubescence: None. J: Shape: Round. K: Bark texture smooth, semi-gloss. L: Bark color: Grey Brown 199B.

*Leaf*.—A. Leaf type: Scale. B. Mature size (L×W): About 2.5 mm×about 3 mm. C. Arrangement on stem: Decussate. D. Aspect: Upright to slightly spreading. E. Color (R.H.S.): Upper — Green 137A; Lower — Green 139C. F. Leaf Number: Average of about 8-10 per cm/stem. G. Apex: Acute-acuminate. H. Base: Rounded. I. Margin: Smooth/Hyaline. J. Shape: Flattened, decussate no lobes present. K. Pubescence: None. L. Venation: None. M. Texture: Waxy, abaxial gland present. O. Odor when crushed: Mild evergreen. P. Winter Discoloration: Greyed-Orange 165B.

*Long shoots*.—A. Facial Gland: Present. B. Leaf Shape: Linear. C. Color: Greyed-orange 177B. D. Tips: Free/acuminate. E. Apex: Acute.

*Coning production*.—None.

*Seed*.—None.

Weather/temperature tolerance: Plants of the new *Thuja* have been observed to grow in USDA Zone 8a, with heat tolerance, and have a USDA Zone range 3-8. 'RutThu5' has also been cold hardy to about −34° F. in trials conducted in Minnesota.

Disease/pest resistance: To date, plants of the new *Thuja* have not been observed to have any diseases or pests in USDA Zone 8a when grown under standard conditions. Specifically, a common fungus, *Passalora* sp., identified on other conifers in USDA Zones 6-8, has not been observed on plants of the new *Thuja* 'RutThu5'.

It is claimed:

1. A new and distinct cultivar of the *Thuja* plant named 'RutThu5' as illustrated and described herein.

* * * * *